United States Patent
Wang et al.

(10) Patent No.: US 11,828,693 B2
(45) Date of Patent: Nov. 28, 2023

(54) CENTRIFUGE METHOD FOR EVALUATING CONTACT ANGLE AND WETTABILITY ALTERATION

(71) Applicant: SAUDI ARABIAN OIL COMPANY, Dhahran (SA)

(72) Inventors: Jinxun Wang, Dhahran (SA); Jun Gao, Dhahran (SA); Abdulkareem Alsofi, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 34 days.

(21) Appl. No.: 17/650,812

(22) Filed: Feb. 11, 2022

(65) Prior Publication Data
US 2023/0258548 A1 Aug. 17, 2023

(51) Int. Cl.
*G01N 13/02* (2006.01)
*G01N 33/24* (2006.01)

(52) U.S. Cl.
CPC .............. *G01N 13/02* (2013.01); *G01N 33/24* (2013.01); *G01N 2013/0208* (2013.01)

(58) Field of Classification Search
CPC . G01N 13/02; G01N 33/24; G01N 2013/0208
USPC .......................................... 73/152.09, 152.11
See application file for complete search history.

(56) References Cited

U.S. PATENT DOCUMENTS

| | | | | |
|---|---|---|---|---|
| 5,069,065 A | * | 12/1991 | Sprunt .................. | G01N 13/00 73/152.09 |
| 5,079,948 A | * | 1/1992 | Collins ................. | G01N 13/00 73/152.24 |
| 5,297,420 A | * | 3/1994 | Gilliland .............. | G01N 33/241 73/38 |
| 5,679,885 A | * | 10/1997 | Lenormand ........... | G01N 29/07 73/152.06 |
| 8,201,439 B2 | | 6/2012 | Szabo et al. | |

(Continued)

OTHER PUBLICATIONS

Morrow, Norman R., "Wettability and Its Effect on Oil Recovery"; Journal of Petroleum Technology; vol. 42, Issue 12, Paper No. SPE-21621-PA; pp. 1476-1484; Dec. 1990 (9 pages).

(Continued)

*Primary Examiner* — John Fitzgerald
(74) *Attorney, Agent, or Firm* — Osha Bergman Watanabe & Burton LLP

(57) ABSTRACT

A method includes saturating a core sample with a hydrocarbon fluid to provide a hydrocarbon-saturated core, placing the core into a first aqueous fluid, applying an external force at increasing magnitude to the hydrocarbon-saturated core to displace a volume of the hydrocarbon fluid in the hydrocarbon-saturated core with the first aqueous fluid at each pressure magnitude, measuring a volume of displaced hydrocarbon fluid at each pressure magnitude, obtaining a first capillary pressure curve, re-saturating the core sample, placing the hydrocarbon-saturated core into a second aqueous fluid having a wettability altering agent, applying an external force at increasing magnitude to displace a volume of the hydrocarbon fluid in the core with the second aqueous fluid at each pressure magnitude, measuring a volume of displaced hydrocarbon fluid at each pressure magnitude, obtaining a second capillary pressure curve, and calculating a contact angle of the second aqueous fluid.

10 Claims, 8 Drawing Sheets

(56) References Cited

U.S. PATENT DOCUMENTS

| | | | | |
|---|---|---|---|---|
| 8,768,628 B2* | 7/2014 | Ghedan | ............... | G01N 33/24 |
| | | | | 166/50 |
| 9,016,111 B2* | 4/2015 | Stukan | ............... | G01N 13/02 |
| | | | | 73/64.48 |
| 11,073,464 B2* | 7/2021 | Gao | ............... | G01N 23/046 |
| 11,187,642 B2* | 11/2021 | Chen | ............... | G01N 15/0806 |
| 11,614,417 B2* | 3/2023 | Gao | ............... | G01N 24/081 |
| | | | | 324/309 |
| 2012/0152547 A1 | 6/2012 | Hinkel | | |
| 2014/0332207 A1* | 11/2014 | Hinkel | ............... | C09K 8/58 |
| | | | | 73/152.05 |

OTHER PUBLICATIONS

Anderson, William G., "Wettability Literature Survery—Part 2: Wettability Measurement"; Journal of Petroleum Technology; vol. 38, Issue 11, Paper No. SPE-13933-PA; pp. 1246-1262; Nov. 1986 (17 pages).

Forbes, P., "Simple and Accurate Methods for Converting Centrifuge Data Into Drainage and Imbibition Capillary Pressure Curves"; The Log Analyst; vol. 35, Issue 4, Paper No. SPWLA-1994-v35n4a3; pp. 31-53; Jul.-Aug. 1994 (23 pages).

Luo, Peng et al., "Simultaneous Capillary Pressure and Wettability Determination for Tight Bakken Cores Using an Ultra-High-Speed Centrifuge"; Proceedings of the SPE Unconventional Resources Conference; Paper No. SPE-185067-MS; pp. 1-15; Feb. 15, 2017 (15 pages).

* cited by examiner

CENTRIFUGE METHOD FOR EVALUATING CONTACT ANGLE AND WETTABILITY ALTERATION

BACKGROUND

Various chemical enhanced oil recovery (EOR) techniques have been developed in order to improve the recovery of hydrocarbon-bearing reservoirs. Wettability alteration is a primary focus in the development of new EOR methods. Traditional flooding compositions may be modified to include wettability alteration agents, that, once downhole, may affect the wetting characteristics of the formation.

As such, laboratory evaluation of formation wettability for specific fluid/fluid systems in reservoir conditions is crucial for reservoir characterization, and in turn, EOR performance prediction. The contact angle between a hydrocarbon fluid and a rock is a physical measurement often used in EOR processes to assess the effect of an injected composition on a downhole system. However, it may be challenging to provide an accurate contact angle measurement for complex fluid systems, such as systems containing wettability alteration agents, as they are designed to lower the interfacial tension between immiscible fluids.

Accordingly, there exists a need for a representative method for contact angle measurement of fluid systems that contain chemical additives.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method that includes saturating a core sample with a hydrocarbon fluid to provide a hydrocarbon-saturated core, placing the hydrocarbon-saturated core into a first aqueous fluid to give a first fluid system, applying an external force at increasing magnitude to the hydrocarbon-saturated core in the first aqueous fluid so as to displace a volume of the hydrocarbon fluid in the hydrocarbon-saturated core with the first aqueous fluid at each pressure magnitude, measuring a volume of displaced hydrocarbon fluid at each pressure magnitude to provide a first set of displaced volumes, obtaining a first capillary pressure curve based on the first set of displaced volume, re-saturating the core sample to provide the hydrocarbon-saturated core, placing the hydrocarbon-saturated core into a second aqueous fluid comprising a wettability altering agent to give a second fluid system, applying an external force at increasing magnitude to the hydrocarbon-saturated core in the second aqueous fluid so as to displace a volume of the hydrocarbon fluid in the hydrocarbon-saturated core with the second aqueous fluid at each pressure magnitude, measuring a volume of displaced hydrocarbon fluid at each pressure magnitude to provide a second set of displaced volumes, obtaining a second capillary pressure curve based on the measured volume of the displaced hydrocarbon fluid, and calculating a contact angle of the second aqueous fluid using the first capillary pressure curve, the second capillary pressure curve, an interfacial tension of the first fluid system, an interfacial tension of the second fluid system, and a contact angle of the first fluid system.

Other aspects and advantages of the claimed subject matter will be apparent from the following description and the appended claims.

DETAILED DESCRIPTION

Embodiments disclosed herein relate to methods and systems for improving contact angle measurement in complex fluid systems to better evaluate wettability alteration. Traditionally, wettability may be measured according to three methods including the Amott method, the USBM (U.S. Bureau of Mines) method, and contact angle measurement. The Amott and USBM methods measure the average wettability of a core sample by evaluating the relative ease of one fluid to displace another. Alternatively, contact angle measurement determines wettability by evaluating the preference of one fluid over another on a specific solid surface. In oil and gas processes, contact angle measurement has long been used as a method for determining the wettability state of reservoirs, and in turn, providing insight into enhanced oil recovery (EOR) based on wettability alteration. Whereas wettability alteration agents, such as surfactants, facilitate EOR, it can be challenging to measure the contact angle of injection fluids that include such agents.

Accordingly, an experimental method to provide representative and quantitative measurements of in situ wettability states is disclosed herein. Methods in one or more embodiments may include determining a contact angle between a hydrocarbon fluid and a reservoir core sample in the presence of an aqueous fluid. In some embodiments, the aqueous fluid may comprise a wettability alteration agent, providing a complex fluid system. Determining the contact angle of a complex fluid system may include measuring other properties of the system relating to wettability, such as capillary pressure (Pc) and interfacial tension (IFT). Methods may further include measuring the same properties of a reference fluid system in which the contact angle is measured, and using the reference properties, in combination with those of the complex fluid system to determine the contact angle of the complex fluid system. This approach may provide an easy method for measuring contact angle and wettability alteration of fluid systems containing various chemical additives.

As described above, the current disclosure relates to a method for measuring contact angle in complex fluid systems. For simple fluid systems, calculating the value of the contact angle between a liquid and a surface may be based on optical measurements of the shape and dimensions of a drop of liquid hydrocarbon deposited on a rock. The drop takes a shape that results from the equilibrium among the forces of gravity, buoyancy, the forces of interfacial tension, adhesion, and the pressure due to the curvature of the interface. By analyzing the shape and dimensions of the drop, it is possible to determine the value of the contact angle in an absolute way.

Figure 1:
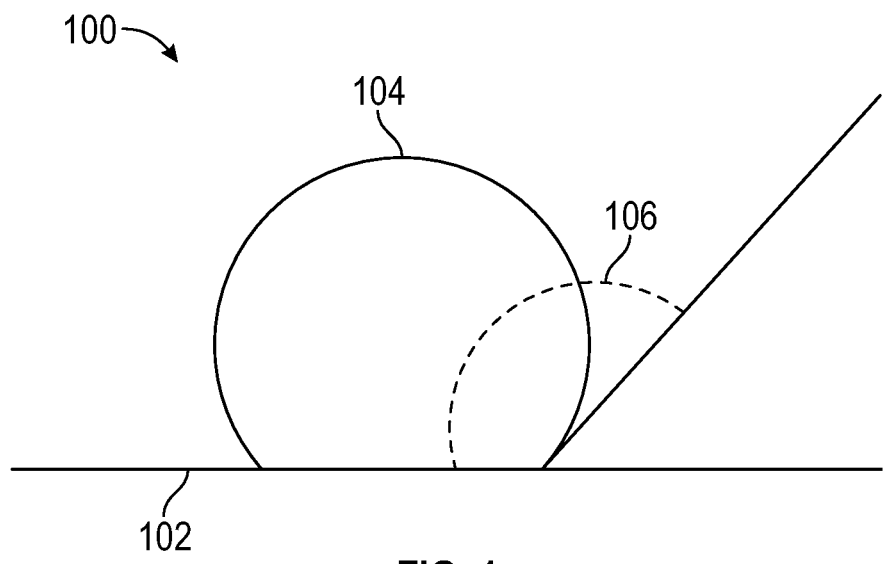
FIG. 1 is a schematic depiction of a set up for contact angle measurement according to one or more embodiments.

FIG. 1 is a schematic depiction of a setup for a contact angle measurement of a simple fluid system 100. As shown, a drop of fluid 104, such as a hydrocarbon, is placed on a surface 102, such as a rock surface from a hydrocarbon bearing formation. When it contacts the surface, it may adhere to or spread out on the surface 102. The drop takes a shape resulting from the aforementioned forces, and a given contact angle θ 106 may be measured. The more the drop spreads out on the surface, the smaller the contact angle, and the higher the wettability. Contact angle measurements can be challenging to conduct for "complex" fluid systems, meaning systems that include more than one fluid, or multiple chemical components in a single fluid. Thus, facile methods of estimating contact angle in complex fluid systems are needed.

In one or more embodiment methods, capillary pressure curves may be used to calculate contact angles of complex fluid systems. In a laboratory environment, capillary pressure is the pressure between two immiscible fluids in a thin tube. The pressure arises from the interactions of the forces between the liquids and solid walls of the tube. In a hydrocarbon formation, capillary pressure results from the combined effect of the interfacial tension between fluids, the pore size and geometry of the pores in the hydrocarbon formation, and the wetting characteristics of the system. If the pore size and geometry are held constant for a reference sample and an experimental sample, the difference in capillary pressure between the two samples depends only on the interfacial tension between fluids and the contact angle of the fluid system on the rock. As such, in one or more embodiments, methods for obtaining capillary pressure curves for a complex fluid system and a reference fluid system may use the same reservoir core sample to ensure uniform pore size and geometry.

Method for Determining Contact Angle of Complex Fluid System

Figure 2:
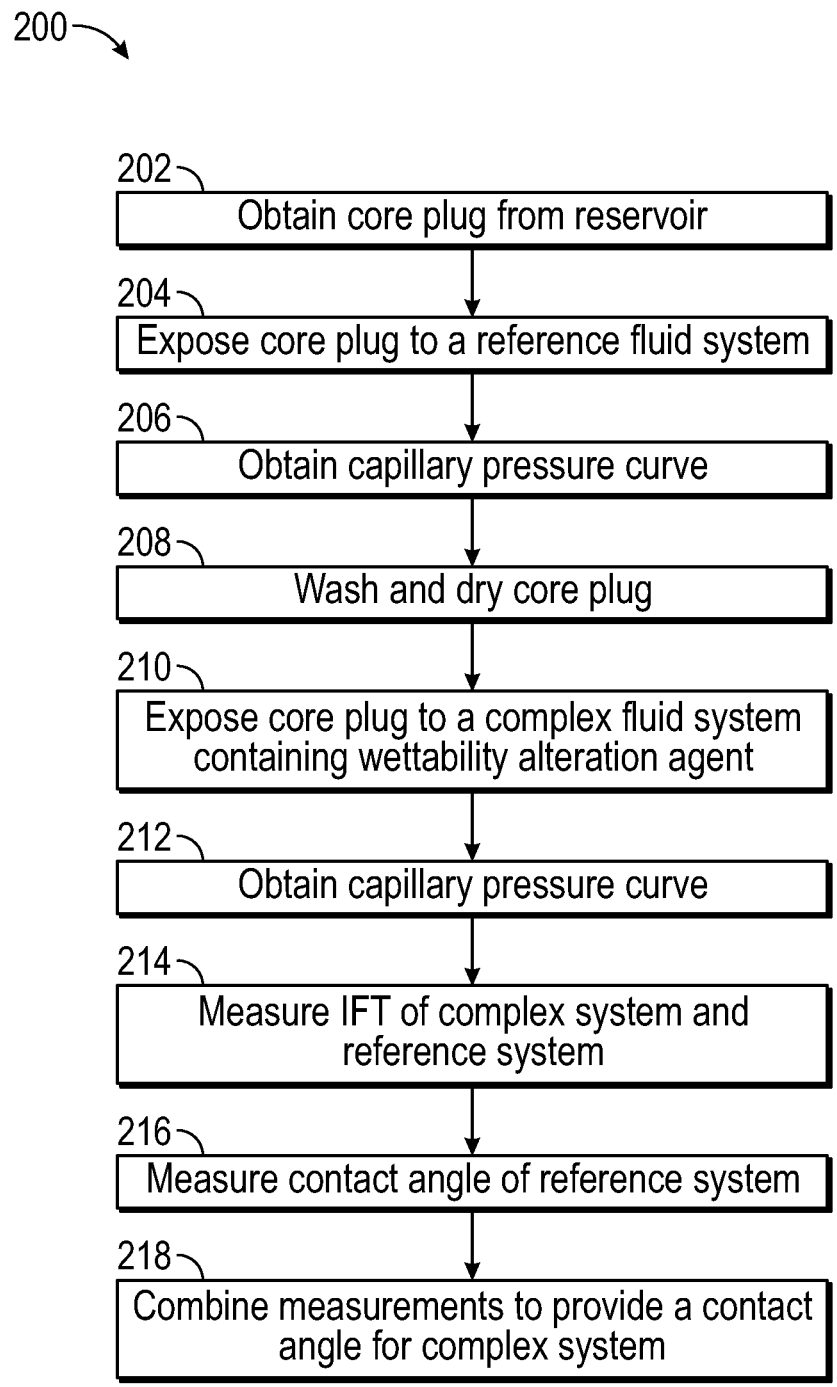
FIG. 2 is a block-flow diagram of a method according to one or more embodiments.

One or more embodiments of the present disclosure relate to methods for determining the contact angle of a complex fluid system. The contact angle of a complex fluid system may be determined using a measured capillary pressure curve and interfacial tension of the system, and then comparing these values to the same properties of a reference system, and the contact angle of the reference system. A method in accordance with one or more embodiments is shown in FIG. 2. The method 200 includes obtaining a core plug from a reservoir 202. The core plug may then be exposed to a reference fluid system comprising a hydrocarbon fluid and an aqueous fluid 204. For this system, the capillary pressure may be measured over a range of pressures, providing a capillary pressure curve 206. After exposure to the reference system, the core plug may be washed and dried 208 to remove any remaining hydrocarbon fluid and aqueous fluid. The plug may then be exposed to a complex fluid system comprising a hydrocarbon fluid and an aqueous fluid that includes a wettability alteration agent 210. A capillary pressure curve may be obtained for this system 212, as noted above. The interfacial tensions of both systems, the reference fluid system and the complex fluid system, may be measured 214. Similarly, the contact angle of the reference system may be measured 216. The above experimental values may then be combined to provide a contact angle of the complex fluid system 218, according to Equation (I) below, $$\cos\theta_c = \frac{P_{cc}}{P_{cr}} \frac{\sigma_r}{\sigma_c} \cos\theta_r \qquad \text{Equation (I)}$$

where $\theta_c$ is the contact angle of the complex system, $\theta_r$ is the contact angle of the reference system, $P_{cc}$ is the capillary pressure of the core containing complex fluid system, $P_{cr}$ is the capillary pressure of the core containing reference fluid system, $\sigma_c$ is the interfacial tension of the complex fluid system and $\sigma_r$ is the interfacial tension of the reference fluid system.

As previously described, embodiment methods include obtaining a core plug from a reservoir 202. The sample may be obtained from any type of reservoir including conventional and unconventional reservoirs, such as sandstone, limestone, shale, and carbonate. In one or more particular embodiments, the core plug is from a carbonate reservoir. Plugs from water-wet reservoirs may not be appropriate for analyses described herein because such reservoirs may not be treated with the presently disclosed wettability alteration agents.

Core plugs may be used directly after being obtained from the reservoir. In some instances, the plugs may be cleaned with solvents to remove oil and salts in the core sample. Suitable solvents for cleaning the core plugs include, but are not limited to, toluene, methanol, and chloroform.

In one or more embodiments, the core plug may be an appropriate size for the disclosed analysis. The plug may have a length ranging from about 2.5 to about 5.0 cm (centimeters). For example, the length of the core plug may have a range having a lower limit of one of 2.5, 2.7, 2.9, 3.0, 3.2, 3.4, 3.6, 3.8 and 4.0 cm and an upper limit of one of 3.6, 3.8, 4.0, 4.2, 4.4, 4.6, 4.8, 4.9, and 5.0 cm, where any lower limit may be combined with any mathematically compatible upper limit. Additionally, the plug may have a diameter ranging from about 2.5 cm to about 3.8 cm. The diameter of the core plug may have a range having a lower limit of one of 2.5, 2.6, 2.7, 2.8, 2.9, and 3.0 cm and an upper limit of one of 3.0, 3.1, 3.2, 3.3, 3.4, 3.5, 3.6, 3.7, and 3.8 cm, where any lower limit may be combined with any mathematically compatible upper limit.

Porosity and permeability are key properties in dictating fluid flow through a given formation and may affect wettability of that formation. As such, the core plug of one or more embodiments may be porous and permeable. Porosity may be expressed as the percentage of pore volume or void space within a rock that contains fluid. The plugs used for the methods disclosed herein may generally have a porosity ranging from about 5% to about 40%. Air permeability generally refers to the measure of air flow through a given medium. The core plugs described herein may have an air permeability ranging from 0.01 to 20,000 and (millidarcies). However, the porosity and permeability values may vary based on the type of core sample being analyzed.

Figure 3:
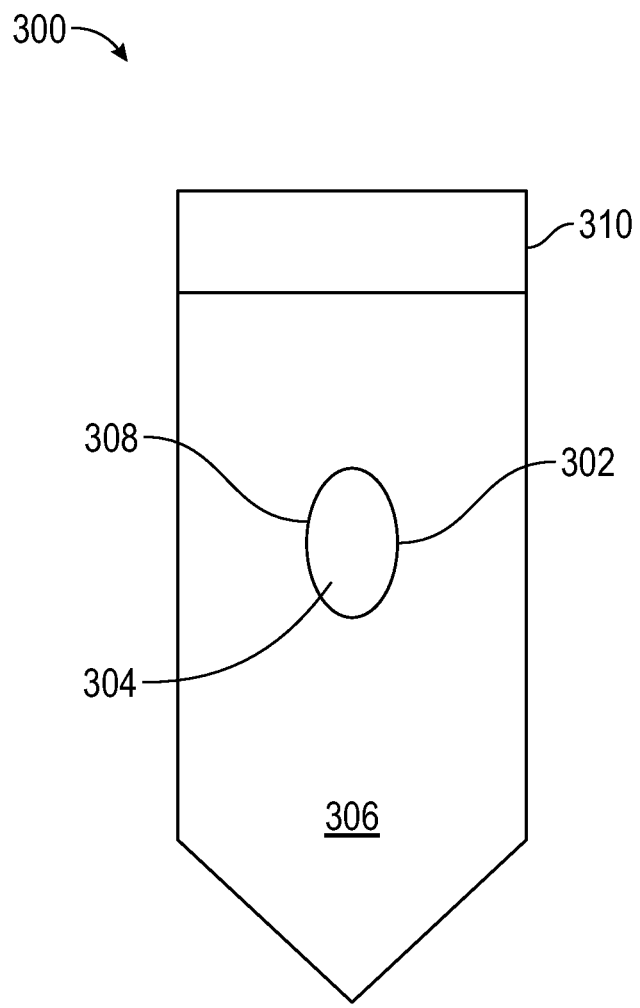
FIG. 3 is a schematic depiction of a reference fluid system according to one or more embodiments.

After the plug has been obtained, it may be exposed to a reference fluid system 204. A schematic description of a core plug in a reference fluid system in accordance with one or more embodiments is shown in FIG. 3. The reference core/fluid system 300 may be prepared as follows. A core plug 302, as previously described, may be saturated in a hydrocarbon fluid 304. The hydrocarbon-saturated core plug 302 may then be placed in a holder 310 that contains an aqueous fluid 306, providing a reference core/fluid system 300. The holder may be any appropriate holder, such as a tube, for the disclosed analysis. In one or more particular embodiments, the holder 310 is a centrifuge tube. In the holder 310, there is a pressure difference across the interface 308 of the hydrocarbon fluid 304 and the aqueous fluid 306. This pressure difference may be referred to as capillary pressure. Capillary pressure is related to the interfacial tension (IFT) between the immiscible liquids, the contact angle of the system, and the pore-throat radius of the core plug 302. A capillary pressure curve may be provided experimentally for the reference core/fluid system 300.

As described above, the core plug 302 may be saturated in a hydrocarbon fluid 304 to provide a hydrocarbon-saturated plug as follows. After the core plug is cleaned and dried, a dry weight may be measured. Then, the core is exposed to a negative pressure, such as a vacuum, to remove the air from the pore space of the dry core plug. The core plug may then saturated with hydrocarbon fluid 304 under vacuum. In order to better simulate downhole conditions, the core plug may first be saturated with formation water. The water may then be displaced with the hydrocarbon fluid so that the core is fully saturated with hydrocarbon fluid. The wet weight of the saturated core plug is measured according to the same method for measuring the dry weight. The level of saturation, or the amount of oil present in the pores of the core, may be determined by the difference between the wet weight and the dry weight of the core plug. The hydrocarbon fluid may contain an oleaginous fluid such as crude oil, condensates, refined oil such as diesel and mineral oil, non-petroleum organics, and combinations thereof.

The hydrocarbon-saturated plug may then be placed in a holder 310 containing aqueous fluid 306. The aqueous fluid 306 of one or more embodiments may include at least one of natural and synthetic water, fresh water, seawater, brine, brackish, formation, production water, and mixtures thereof. The aqueous fluid may be fresh water that is formulated to contain various salts. The salts may include, but are not limited to, alkali metal and alkaline earth metal halides, hydroxides, carbonates, bicarbonates, sulfates, and phosphates. In one or more embodiments, the brine may be any of seawater, aqueous solutions where the salt concentration is less than that of seawater, or aqueous solutions where the salt concentration is greater than that of seawater. Salts that may be found in brine may include salts that produce disassociated ions of sodium, calcium, aluminum, magnesium, potassium, strontium, lithium, halides, carbonates, bicarbonates, sulfates, chlorates, bromates, nitrates, oxides, and phosphates, among others. In some embodiments, the brine may include one or more of an alkali metal halide, an alkali metal sulfate salt, an alkaline earth metal halide, and an alkali metal bicarbonate salt. In particular embodiments, the brine may comprise one or more of sodium chloride, calcium chloride, magnesium chloride, sodium sulfate, and sodium bicarbonate. Any of the aforementioned salts may be included in brine.

The aqueous fluid of one or more embodiments may have a total dissolved solids (TDS) of 1,000 milligrams per liter (mg/L) or more, 10,000 mg/L or more, 50,000 mg/L or more, or 100,000 mg/L or more. In some embodiments, the aqueous fluid may have a TDS of an amount of a range having a lower limit of any of 1,000, 5,000, 10,000, 30,000, 50,000, and 55,000 mg/L and an upper limit of any of 50,000, 55,000, 60,000, 65,000, 75,000, 100,000, 150,000, 200,000, 250,000, and 350,000 mg/L, where any lower limit can be used in combination with any mathematically compatible upper limit. A person of ordinary skill in the art would appreciate with the benefit of this disclosure that the density of aqueous fluid may be affected by the salt concentration of the aqueous fluid. The maximum concentration of a given salt is determined by its solubility.

Figure 4:
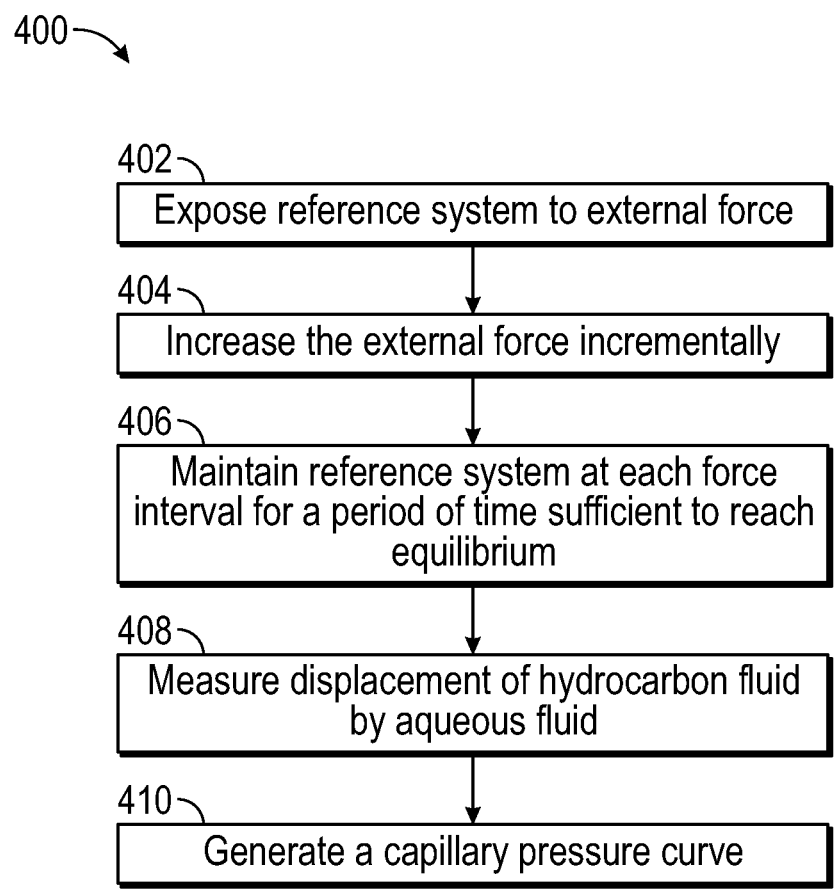
FIG. 4 is a block-flow diagram of a method for obtaining a capillary curve according to one or more embodiments.

The amount of force it takes to displace the hydrocarbon fluid 304 from the core plug 302 with the aqueous fluid 306 may be equated to the capillary pressure. As such, a capillary pressure curve may be provided, and a final capillary pressure determined for the reference core/fluid system 300. FIG. 4 shows a block-flow diagram of the method for obtaining a capillary pressure curve 400 in accordance with one or more embodiments.

In order to obtain a capillary pressure curve, the reference core/fluid system 300 of FIG. 3 may be exposed to an external force 402. In one or more particular embodiments, a centrifuge is used to apply the external force on the system. In such embodiments, force is determined by the rotation speed of the centrifuge.

The external force may be incrementally increased 404. In embodiments in which a centrifuge is used to apply force, the force may be increased by increasing the rotation speed of the centrifuge. At each force interval, a strobe light may be used to detect the fluid interfaces, and thus, the volume of hydrocarbon fluid that has been displaced by the first aqueous fluid may be measured 406. As will be appreciated by those skilled in the art, various commercially available centrifuges may be equipped with strobe lights to aid in viewing samples. Thus, a strobe light may be used to view the fluid interfaces and determine the volume of displaced hydrocarbon fluid. The reference core/fluid system may be exposed to each interval of force for a time sufficient for an equilibrium within the system to be reached 408. Different criteria for reaching an equilibrium may depend on the specific core/fluid system. In an exemplary case, each rotational speed may be continued until the amount of the produced fluid has been reduced to an average of about 0.001 pore volume per hour (vol/h) or less over a period of at least 8 hours (h). As such, the time at each speed to reach equilibrium may range from 24 to 72 h, depending on the specific core/fluid system. A capillary pressure curve may then be generated as a function of capillary pressure (or external force applied) vs the fraction of aqueous fluid saturation of the core plug 410. The average aqueous fluid saturation at each force interval may be determined based on the produced oil and the pore volume of the core plug. An average aqueous fluid saturation is used because the aqueous fluid saturation, along with the capillary pressure, varies along the core plug. The values at the inner-face (the face of the plug closest to the external force) may be used to calculated the capillary pressure. Similarly, the end-face aqueous fluid saturation may be calculated from the average aqueous fluid saturation according to methods known in the art such as Forbes first and Forbes second methods, among others.

As previously described, the external force may be incrementally increased. In one or more embodiments, the external force may be increased over a range of about 0.5 to 450 psi (pounds per square inch). For example, the external force applied to a system may be increased over a range of 0.5 to 450 psi, 0.5 to 350 psi, 0.5 to 250 psi, 0.5 to 150 psi, and 0.5 to 50 psi. The external force may be increased by increments ranging from 2 to 10 psi. The external force may be increased by an increment range having a lower limit of one of 2, 3, 4, 5, and 6 psi and an upper limit of one of 5, 6, 7, 8, 9, and 10 psi, where any lower limit may be combined with any mathematically compatible upper limit.

Subsequent to obtaining a capillary pressure curve for a reference core/fluid system, the core plug may be washed and dried, so that it may be exposed to a complex core/fluid system. One or more embodiment methods include washing the core plug with a hydrophobic organic fluid to remove any remaining hydrocarbon fluid. Suitable hydrophobic organic fluids include, but are not limited to, toluene, chloroform, methanol, ethanol, acetone, pentane, hexanes, heptane, and combinations thereof. The plug may then be washed with a polar solvent so as to remove any remaining salts. Examples of polar solvents that may be used to wash the core include methanol, ethanol, isopropanol, among others. The core plug may then be placed in an oven at a temperature ranging from 60° C. to 105° C. until sufficiently dry. Depending on the size of the core plug, it may take anywhere from 48 to 96 hours for the sample to be sufficiently dry.

Figure 5:
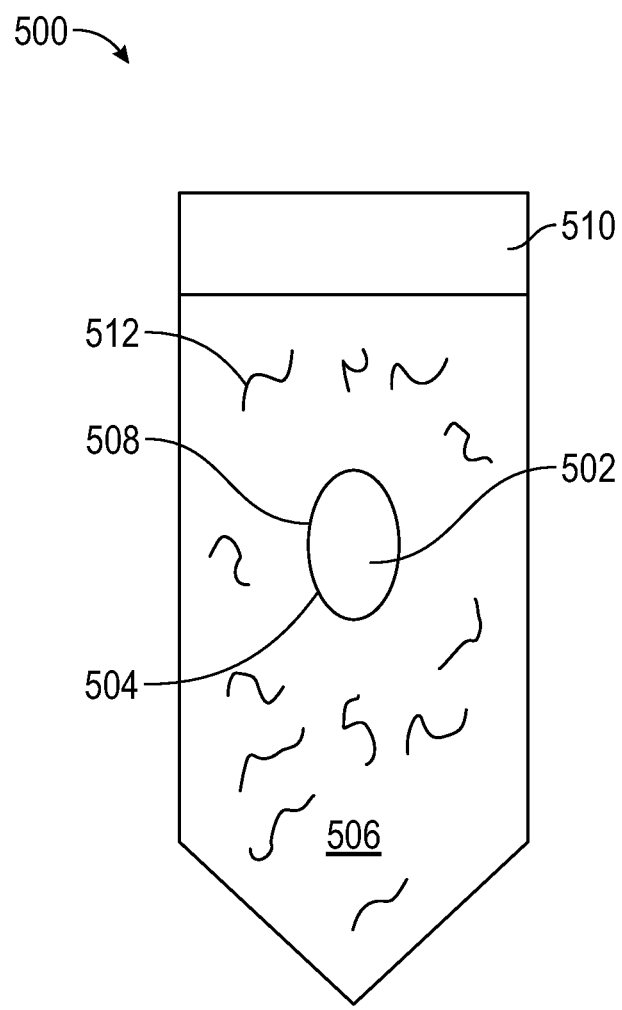
FIG. 5 is a schematic depiction of a complex fluid system according to one or more embodiments.

The dried core plug may then be exposed to a complex fluid system to provide a complex core/fluid system, as depicted schematically in FIG. 5. The complex core/fluid system 500 may be prepared as follows. A core plug 502, as previously described, may be saturated in a hydrocarbon fluid 504. The hydrocarbon-saturated plug may then be placed in a tube 510 that contains an aqueous fluid 506. The aqueous fluid 506 may comprise a wettability alteration agent 512, as such, providing a complex core/fluid system 500. In one or more embodiments the wettability alteration agent may be a surfactant. The surfactant may be any surfactant potentially useful in enhanced oil recovery applications. The surfactant may be non-ionic, cationic, anionic, zwitterionic, catanionic, gemini and combinations thereof. Exemplary surfactants include, but are not limited to, betaine-type amphoteric surfactants such as alkyl dimethyl betaine, cetyl dimethyl carboxymethyl betaine, erucyl dimethyl betaine sulfonate; anionic surfactants such as alcohol alkoxy sulfate, alpha olefin sulfonate, internal olefin sulfonate; cationic surfactants such as cetyl trimethyl ammonium bromide (CTAB), quaternary ammonium, ethoxylated alkyl amine; nonionic surfactants such as alcohol ethoxylates, aykyl ethoxy carboxylate, alkyl polyglucosides.

The wettability alteration agent 512 may be present in the aqueous fluid 506 in an amount ranging from 500 parts per million (ppm) to 5,000 ppm. For example, the aqueous fluid may include a wettability alteration agent in an amount having a lower limit of one of 500, 550, 750, 900, 1,000, 1,500, and 2,000 ppm and an upper limit of one of 2,000, 2,500, 3,000, 3,500, 4,000, 4,500 and 5,000 ppm, where any lower limit may be combined with any mathematically compatible upper limit.

As described above for the reference core/fluid system, a capillary pressure exists at the interface 508 of the hydrocarbon fluid 504 and the second aqueous fluid 506, in the complex core/fluid system 500. A capillary pressure curve may be provided experimentally for the complex core/fluid system 500, according to the method described above for the reference core/fluid system 300 (referring to FIG. 3).

Capillary pressure is related to the interfacial tension (IFT) between immiscible liquids of a system, the contact angle of a system, and the pore-throat radius of a core plug according to the following Equation (II):

$$P_c = \frac{2\sigma\cos\theta}{r} \quad \text{Equation (II)}$$

where $P_c$ is the capillary pressure, $\sigma$ is the IFT, $\theta$ is the contact angle, and r is the pore-throat radius. For two separate systems with a core plug having the same pore-throat radius, as is described in embodiments herein, Equation (II) may be combined to give Equation (I) as follows:

$$\cos\theta_c = \frac{P_{cc}}{P_{cr}} \frac{\sigma_r}{\sigma_c} \cos\theta_r \quad \text{(I)}$$

where $\theta_c$ is the contact angle of the complex core/fluid system, $\theta_r$ is the contact angle of the reference core/fluid system, $P_{cc}$ is the capillary pressure of the complex core/fluid system, $P_{cr}$ is the capillary pressure of the reference core/fluid system, $\sigma_c$ is the interfacial tension of the complex fluid system and $\sigma_r$ is the interfacial tension of the reference fluid system.

Therefore, in order to calculate a contact angle for a complex core/fluid system in accordance with one or more embodiments, methods may include measuring the interfacial tension between the hydrocarbon fluid and the first aqueous fluid of the reference fluid system. The interfacial tension between two immiscible fluids is largely a result of the adhesive forces experienced at the interface of the fluids. If adhesive forces between two fluids are weak, the IFT will be high, whereas strong adhesive forces result in a low IFT between two fluids. The interfacial tension of a reference fluid system according to the present disclosure may be measured using methods known in the art, such as the pendant drop method. In such methods, the shape of a drop of fluid hanging from a needle is determined and the interfacial tension is calculated using known equations. For example, the pendant drop method may be conducted using the Drop Shape Analysis System provided by KRÜSS GmbH, Germany.

In one or more embodiments, the IFT of a reference fluid system may range from 5 to 30 mN/m (milliNewtons/meter). For example, the IFT between a hydrocarbon fluid and an aqueous fluid without a wettability alteration agent may have a range having a lower limit of any of 5, 7, 10, 12, 15, 17, and 20 mN/m and an upper limit of any of 15, 17, 20, 22, 25, 27, and 30 mN/m, where any lower limit may be combined with any mathematically compatible upper limit.

Methods may also include measuring the interfacial tension between the hydrocarbon fluid and the second aqueous fluid that contains a wettability alteration agent of the complex fluid system. Due to the presence of a wettability alteration agent in the second aqueous fluid, the IFT of a complex fluid system may be lower than that of a reference fluid system. The IFT between the fluids of a complex fluid system may range from about 0.001 mN/m to 5 mN/m. The IFT of a complex fluid system may have a range having a lower limit of any of 0.001, 0.005, 0.01, 0.025, 0.05, 0.075, 0.1, 0.15, 0.2, 0.25, 0.3, 0.35, 0.5, and 1 and an upper limit of any of 0.5, 1.0, 1.5, 2.0, 2.5, 3.0, 3.5, 4.0, 4.5, and 5.0, where any lower limit may be combined with any mathematically compatible upper limit.

In one or more embodiment methods, the contact angle of the reference fluid system may be measured. Since the reference fluid system does not contain a wettability alteration agent, the contact angle may be measured according to conventional methods known in the art. For example, the contact angle of the reference fluid system may be measured by methods including the captive drop method, the Wilhelmy plate method, and the capillary rise method, among others.

One or more embodiment methods include combining the above measurements including, for the reference fluid system: the IFT, the contact angle, and the capillary pressure curve, and for the complex fluid system: the IFT and the capillary pressure curve, to provide a contact angle for the complex fluid system.

In one or more embodiments, after calculating the contact angle of the complex fluid as previously described, the aqueous fluid of the complex fluid described above may be used to treat a hydrocarbon-bearing formation. In one or more embodiments, the using may comprise introducing an oil recovery composition comprising a wettability altering agent such as a surfactant into a hydrocarbon-bearing formation. Oil recovery compositions in accordance with the present disclosure may be any type of oil recovery composition that includes a wettability altering agent. In one or more embodiments, the oil recovery composition comprising the wettability altering agent may be an aqueous composition for use in water flooding. In such embodiments, the wettability altering agent may be mixed with an aqueous component, such as seawater, and then introduced into the hydrocarbon-bearing formation as an aqueous composition.

Figure 6:
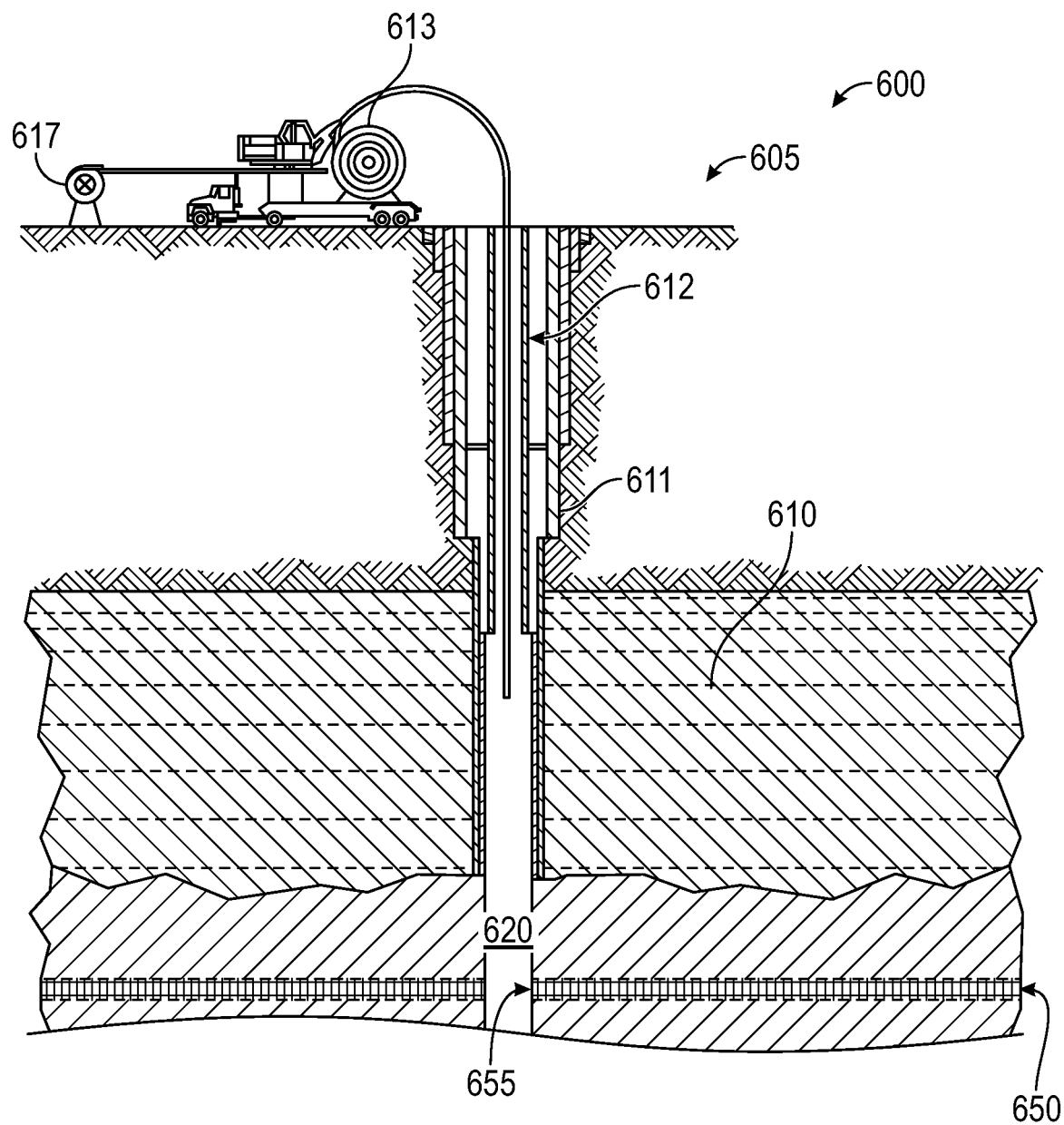
FIG. 6 is a schematic depiction of a well environment according to one or more embodiments.

FIG. 6 is a diagram that illustrates a well environment 600 in accordance with one or more embodiments. Well environment 600 includes a subsurface 610. Subsurface 610 is depicted having a wellbore wall 611 both extending downhole from a surface 605 into the subsurface 610 and defining a wellbore 620. The subsurface also includes target formation 650 to be treated. Target formation 650 has target formation face 655 that fluidly couples target formation 650 with wellbore 620 through wellbore wall 611. In this case, casing 612 and coiled tubing 613 extend downhole through the wellbore 620 into the subsurface 610 and towards target formation 650. With the configuration in FIG. 6, the previously described oil recovery composition may be introduced into the subsurface 610 and towards target formation 650 via a pump 617 through the coiled tubing 613.

Figure 8:
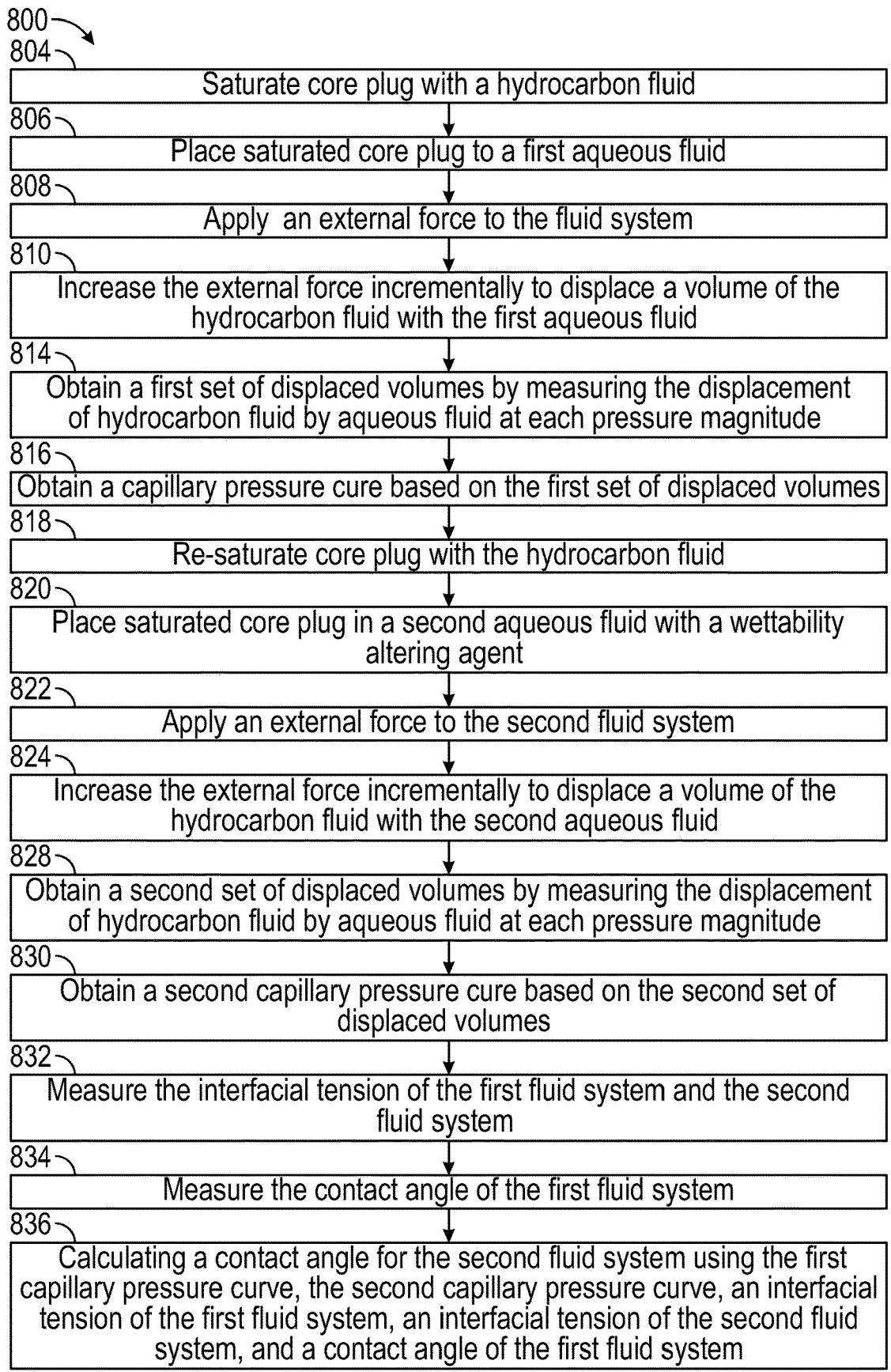
FIG. 8 is a block-flow diagram of a method according to one or more embodiments.

In one or more embodiment methods, as shown in FIG. 8, the method includes saturating a core sample with a hydrocarbon fluid to provide a hydrocarbon-saturated core (804). Then placing the hydrocarbon-saturated core into a first aqueous fluid to give a first fluid system (806) and applying an external force (808) at increasing magnitude (810) to the hydrocarbon-saturated core in the first aqueous fluid so as to displace a volume of the hydrocarbon fluid in the hydrocarbon-saturated core with the first aqueous fluid at each pressure magnitude. The volume of displaced hydrocarbon fluid at each pressure magnitude is then measured to provide a first set of displaced volumes (814). A first capillary pressure curve is then obtained based on the first set of displaced volumes (816). Then the core sample is re-saturated to provide the hydrocarbon-saturated core (818) and the hydrocarbon-saturated core is placed into a second aqueous fluid comprising a wettability altering agent to give a second fluid system (820). An external force (822) is applied at increasing magnitude (824) to the hydrocarbon-saturated core in the second aqueous fluid so as to displace a volume of the hydrocarbon fluid in the hydrocarbon-saturated core with the second aqueous fluid at each pressure magnitude. The method then involves measuring a volume of displaced hydrocarbon fluid at each pressure magnitude to provide a second set of displaced volumes (828) and obtaining a second capillary pressure curve based on the measured volume of the displaced hydrocarbon fluid (830). Finally, a contact angle (836) of the second aqueous fluid is calculated using the first capillary pressure curve, the second capillary pressure curve, an interfacial tension of the first fluid system (832), an interfacial tension of the second fluid system, and a contact angle of the first fluid system (834).

Hydrocarbon-bearing formations may include any oleaginous fluid, such as crude oil, dry gas, wet gas, gas condensates, light hydrocarbon liquids, tars, and asphalts, and other hydrocarbon materials. Hydrocarbon-bearing formations may also include aqueous fluid, such as water and brines. Embodiment oil recovery compositions may be appropriate for use in different types of subterranean formations, such as carbonate, shale, sandstone and tar sands.

Embodiment methods of the present disclosure may provide a quantitative measurement and a more representative method for evaluating in situ wettability. Contact angle is challenging to measure in complex fluid systems, in which the aqueous phase contains chemical agents. Methods herein may provide more accurate wettability measurements, such as contact angle, for complex fluid systems with low interfacial tension.

EXAMPLES

Capillary pressure curves for two carbonate core plugs, 1 and 2 were obtained. The properties of the core plugs are included in Table 1 below. The porosity was measured using an UltraPore Porosimeter form Core Lab Instruments. Porosity measurements were obtained using helium gas. The permeability was measured using nitrogen gas in an Ultra-Perm Gas Permeameter from Core Lab Instruments.

TABLE 1

Properties of Core Plug Samples

| Core Plug | Length (cm) | Diameter (cm) | Porosity (%) | Air Permeability (md) |
|---|---|---|---|---|
| 1 | 4.879 | 3.764 | 28.1 | 140 |
| 2 | 4.926 | 3.746 | 32.4 | 169 |

Core plugs 1 and 2 were used to test the reference and complex systems, and the contact angle of the complex system was determined for both plugs.

Core plugs were saturated with a crude oil sampled from an oil reservoir. First, the air was removed from the pores of the plugs using a vacuum. Then, the core was saturated with the crude oil at room temperature. At room temperature (23° C.), the crude oil has a density of 0.868 g/cm$^3$.

A synthetic brine, with 57,670 mg/L total dissolved solids (TDS), was used in these examples as the aqueous fluid, and its composition is included in Table 2. At room temperature (23° C.), the synthetic brine had a density of 1.038 g/cm$^3$.

TABLE 2

Composition of Synthetic Brine

| Salt | Amount (mg/L) |
|---|---|
| Na$^+$ (mg/L) | 18,300 |
| Ca$^{2+}$ (mg/L) | 650 |
| Mg$^{2+}$ (mg/L)) | 2,110 |
| Cl$^-$ (mg/L) | 32,200 |
| HCO$_3^-$ (mg/L) | 120 |
| SO$_4^{2-}$ (mg/L) | 4,290 |
| TDS (mg/L) | 57,670 |

The surfactant used in these examples was a betaine-type amphoteric surfactant provided by Oil Chem Technologies (USA). The molecular weight of the surfactant was 430 g/mol. The surfactant was added to the synthetic brine to achieve a surfactant concentration of 2,000 ppm.

The interfacial tension between the oil and synthetic brine was measured by pendant drop method using a Surface Tensiometer from Kruss Germany. The average measured IFT between the oil and synthetic brine (i.e., the reference fluid system) was 17.8 mN/m at 23° C. The IFT between the oil and surfactant solution was measured by a Spinning Drop Tensiometer from Kruss Germany. The measured IFT between the oil and the surfactant solution (i.e., the complex fluid system) is 0.097 mN/m at 23° C.

A cleaned rock chip was cut from the same whole core as used for sampling the plugs for the capillary pressure test. The rock chip had a size of about 2.2 cm×2.2 cm×0.5 cm. The rock surface was polished to minimize the contact angle hysteresis due to surface roughness. The same cleaning procedure for core plugs described above was used to clean the rock chip. The rock chip was fully saturated with brine, and then used to measure the contact angle of reference core/fluid system using the conventional captive drop method. A Drop Shape Analysis System from Kruss Germany was used to measure the contact angle. The prepared rock chip was first horizontally placed in the test cell, and the cell was then fully filled with the synthetic brine. The oil drop was generated using a needle through a minidosing syringe, and then brought to contact the flat rock surface from its bottom. The drop image was captured using a camera and the contact angle was analyzed by a computer. At room temperature, the measured contact angle was 86°.

Two rounds of centrifuge testing were conducted on the core samples at room temperature. The reference system centrifuge test was performed first. The core plugs were first 100 percent saturated with oil, and then placed into centrifuge tubes that were filled with the synthetic brine. The tubes were loaded into a centrifuge apparatus, and the samples were spun continuously at incrementally increased rotation speeds. The test was conducted at nine rotation speeds: 250, 400, 650, 950, 1350, 1850, 2500, 4500, and 4500 rpm (rotations per minute). Sufficient time was allowed at each rotation speed for equilibrium condition to be achieved within the samples. The volumes of oil displaced by water from the core samples at each speed were measured using a strobe light and the obtained values were recorded.

After the reference system centrifuge test, core samples were cleaned using a Dean Stark Apparatus with toluene to remove all the oil, followed by methanol cleaning to remove all the salts in the cores. Then, the core plugs were fully dried in an oven at 95° C. for 48 h, and re-saturated with oil for the second round of centrifuge testing with the complex core/fluid system. The procedure was the same as for the reference system centrifuge test, but the oil-saturated core samples were centrifuged in the 2,000 ppm surfactant solution. Similarly, the volumes of oil displaced by the surfactant solution from the core samples at each speed were recorded for determining the capillary pressure curves.

Figure 7A:
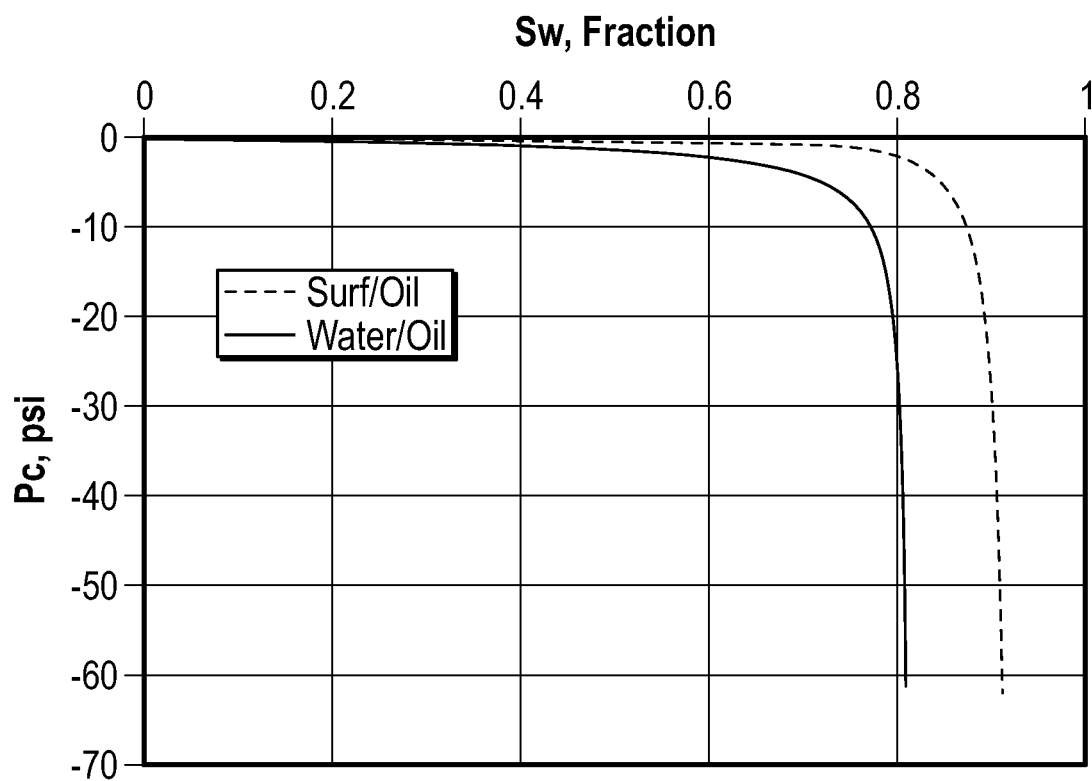
FIG. 7A is a graph of capillary curves according to one or more embodiments.
Figure 7B:
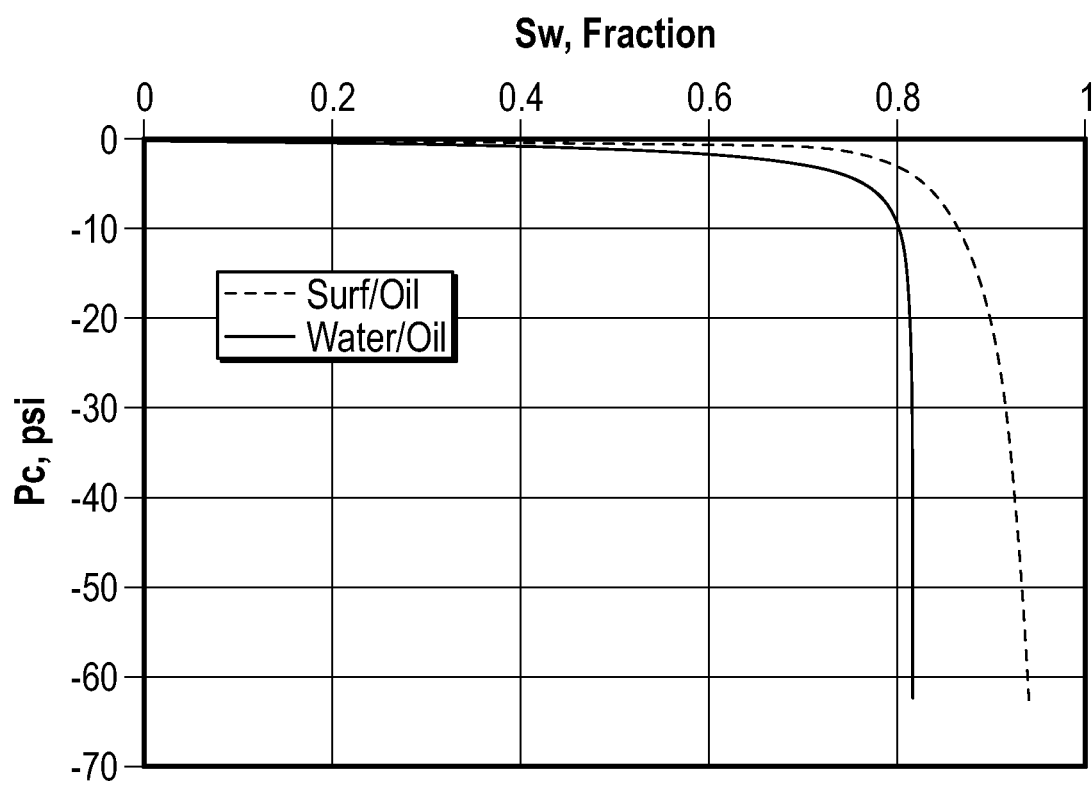
FIG. 7B is a graph of capillary curves according to one or more embodiments.

The capillary pressure curves (capillary pressure as a function of water saturation) were determined from the displacement volumes and the equivalent pressures applied through the different rotation speeds. The end-face water saturation was calculated from the average saturation by using Forbes first method. Capillary pressure curves generated for both fluid systems for core plug 1 are shown in FIG. 7A. Capillary pressure curves generated for both fluid systems for core plug 2 are shown in FIG. 7B.

Combining the capillary pressure results, the IFTs of the two fluid systems and the contact angle of the reference core/fluid system, the contact angle of the complex core/fluid was determined using Equation (I), from above. The capillary pressure values at the highest water saturation that each system reached were used in the calculations. The estimated contact angle results for Samples 1 and 2 were 52.4° and 34.3°, respectively.

The wettability preference is commonly evaluated by the criterion used in oil and gas applications. When the contact angle is between 0° and 60 to 75°, it is water-wet system. When the contact is between 180° and 105 to 120°, it is oil-wet system. In the middle range of contact angle, from a low cutoff limit of 60 to 75° to a high cutoff limit of 105 to 120°, the system is intermediately wet. In both examples, the contact angle of the reference core/fluid system was 86°, which is an intermediate-wet condition. For the complex core/fluid system, the contact angle results of 52.4° and 34.3° indicate that the surfactant altered the wettability to a water-wet condition.

Although only a few example embodiments have been described in detail above, those skilled in the art will readily appreciate that many modifications are possible in the example embodiments without materially departing from this invention. Accordingly, all such modifications are intend to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:
1. A method comprising:
saturating a core sample with a hydrocarbon fluid to provide a hydrocarbon-saturated core;
placing the hydrocarbon-saturated core into a first aqueous fluid to give a first fluid system;
applying an external force at increasing magnitude to the hydrocarbon-saturated core in the first aqueous fluid so as to displace a volume of the hydrocarbon fluid in the hydrocarbon-saturated core with the first aqueous fluid at each pressure magnitude;
measuring a volume of displaced hydrocarbon fluid at each pressure magnitude to provide a first set of displaced volumes;
obtaining a first capillary pressure curve based on the first set of displaced volumes;
re-saturating the core sample to provide the hydrocarbon-saturated core;
placing the hydrocarbon-saturated core into a second aqueous fluid comprising a wettability altering agent to give a second fluid system;
applying an external force at increasing magnitude to the hydrocarbon-saturated core in the second aqueous fluid so as to displace a volume of the hydrocarbon fluid in the hydrocarbon-saturated core with the second aqueous fluid at each pressure magnitude;
measuring a volume of displaced hydrocarbon fluid at each pressure magnitude to provide a second set of displaced volumes;

obtaining a second capillary pressure curve based on the measured volume of the displaced hydrocarbon fluid; and calculating a contact angle of the second aqueous fluid using the first capillary pressure curve, the second capillary pressure curve, an interfacial tension of the first fluid system, an interfacial tension of the second fluid system, and a contact angle of the first fluid system.

2. The method of claim 1, wherein the hydrocarbon fluid is selected from the group consisting of crude oil, condensates, diesel, mineral oil, non-petroleum organics, and combinations thereof.

3. The method of claim 1, wherein the first aqueous fluid is a brine.

4. The method of claim 1, wherein the external force is applied by centrifugation.

5. The method of claim 4, wherein the centrifugation is conducted at a plurality of increasing rotational speeds.

6. The method of claim 1, wherein the second aqueous fluid includes a surfactant.

7. The method of claim 6, wherein the surfactant is a selected from the group consisting of a non-ionic surfactant, a cationic surfactant, an anionic surfactant, a zwitterionic surfactant, a catanionic surfactant, a gemini surfactant and combinations thereof.

8. The method of claim 1, further comprising:

measuring a first interfacial tension of the first fluid system comprising the first aqueous fluid and a second interfacial tension of the second fluid system comprising the second aqueous fluid.

9. The method of claim 1, further comprising, measuring a first contact angle of the first fluid system.

10. The method of claim 1, further comprising, after calculating the contact angle of the second aqueous fluid, using the second aqueous fluid to treat a hydrocarbon-bearing formation, wherein the using comprising introducing an oil recovery composition comprising the wettability alteration agent into the hydrocarbon-bearing formation.

* * * * *